United States Patent
Aspinall (10) Patent No.: US 10,234,361 B2
(45) Date of Patent: Mar. 19, 2019

(54) HEAT EXCHANGER TESTING DEVICE

(71) Applicant: Knew Value, LLC, Huffman, TX (US)

(72) Inventor: Laurin Joseph Aspinall, Huffman, TX (US)

(73) Assignee: Knew Value LLC, Huffman, TX (US)

( * ) Notice: Subject to any disclaimer, the term of this patent is extended or adjusted under 35 U.S.C. 154(b) by 0 days.

(21) Appl. No.: 15/724,046

(22) Filed: Oct. 3, 2017

(65) Prior Publication Data

US 2018/0024028 A1 Jan. 25, 2018

Related U.S. Application Data (63) Continuation-in-part of application No. 14/321,244, filed on Jul. 1, 2014, now Pat. No. 9,778,147.

(Continued)

(51) Int. Cl.
*G01M 99/00* (2011.01)
*F28D 7/06* (2006.01)
(Continued)

(52) U.S. Cl.
CPC .............. *G01M 99/002* (2013.01); *F28D 7/06* (2013.01); *F28F 1/00* (2013.01); *G01M 99/008* (2013.01);
(Continued)

(58) Field of Classification Search
CPC .......... G01K 17/00; G01N 3/18; G01N 25/72; G01N 25/145; G01M 99/00; F01K 11/04; F02G 1/055; F28D 7/06
See application file for complete search history.

(56) References Cited

U.S. PATENT DOCUMENTS 3,921,436 A 11/1975 Plegat
4,044,605 A 8/1977 Bratthall
(Continued)

FOREIGN PATENT DOCUMENTS

DE 29607030 4/1996
DE 19854773 11/1998
(Continued)

OTHER PUBLICATIONS

European Search Report, dated Feb. 15, 2017 for Appl. No. 14820461.3-1557.
(Continued)

*Primary Examiner* — Gail Kaplan Verbitsky
(74) *Attorney, Agent, or Firm* — Greer, Burns & Crain Ltd.

(57) ABSTRACT

An apparatus and a process for testing fluid from a heat exchanger. A first fluid from a heat exchanger to be tested is passed through a test heat exchanger. A second, heat transfer fluid, is in the test heat exchanger. The second fluid is heated with a heater so that a temperature in the test heat exchanger can be controlled, for example, to so that conditions in the heat exchanger are close to the conditions in the heat exchanger. After a period of time, the test heat exchanger can be removed and inspected, tested, or both. Also, multiple test heat exchangers may be used to test various process conditions. Additionally, the test heat exchangers may include different materials to test various materials. An outer portion of the test heat exchanger may be at least semi-transparent.

17 Claims, 11 Drawing Sheets

Related U.S. Application Data (60) Provisional application No. 61/841,643, filed on Jul. 1, 2013.

(51) Int. Cl.
  G01N 25/72 (2006.01)
  F28F 1/00 (2006.01)
  G01N 25/14 (2006.01)

(52) U.S. Cl.
  CPC ........... G01N 25/145 (2013.01); G01N 25/72 (2013.01); *F28F 2200/00* (2013.01)

(56) References Cited

U.S. PATENT DOCUMENTS

| | | | |
|---|---|---|---|
| 4,097,341 A | 6/1978 | Schell et al. | |
| 4,339,945 A | 7/1982 | Knudsen et al. | |
| 4,383,438 A | 5/1983 | Eaton | |
| 4,554,969 A | 11/1985 | Carnavos | |
| 4,686,853 A | 8/1987 | Sugam et al. | |
| 4,813,270 A | 3/1989 | Baillie | |
| 4,906,307 A | 3/1990 | Fujiyoshi | |
| 5,083,606 A | 1/1992 | Brown et al. | |
| 5,174,654 A * | 12/1992 | Droege | G01K 17/20 165/11.1 |
| 5,215,704 A | 6/1993 | Hirota | |
| 5,353,653 A | 10/1994 | Watanabe et al. | |
| 6,241,383 B1 | 6/2001 | Feller et al. | |
| 6,499,876 B1 | 12/2002 | Baginski et al. | |
| 6,678,628 B2 | 1/2004 | Ryan et al. | |
| 7,051,801 B1 * | 5/2006 | Cargnelli | H01M 8/04014 165/228 |
| 8,091,621 B2 * | 1/2012 | Zobel | B21C 37/151 165/177 |
| 9,534,856 B2 | 1/2017 | Suzuki et al. | |
| 2005/0160742 A1 * | 7/2005 | Naaman | B60H 1/00478 62/3.2 |
| 2006/0021739 A1 | 2/2006 | Young et al. | |
| 2006/0249020 A1 | 11/2006 | Tonkovich et al. | |
| 2007/0169477 A1 * | 7/2007 | Mori | F02B 61/00 60/520 |
| 2007/0209365 A1 | 9/2007 | Hamer et al. | |
| 2007/0228113 A1 | 10/2007 | Dupree et al. | |
| 2008/0285616 A1 | 11/2008 | Nakanishi et al. | |
| 2009/0087903 A1 | 4/2009 | Belgrader et al. | |
| 2009/0173336 A1 | 7/2009 | Leifer et al. | |
| 2010/0036638 A1 | 2/2010 | Friedrich et al. | |
| 2011/0283736 A1 | 11/2011 | Manabe et al. | |
| 2013/0118706 A1 | 5/2013 | Kareh et al. | |
| 2013/0340976 A1 | 12/2013 | Karniyarna et al. | |
| 2014/0008035 A1 | 1/2014 | Patankar et al. | |
| 2014/0021673 A1 | 1/2014 | Chen et al. | |
| 2014/0341256 A1 | 11/2014 | Azeem et al. | |
| 2015/0101334 A1 | 4/2015 | Bond et al. | |
| 2015/0168073 A1 | 6/2015 | Bugler, III et al. | |
| 2015/0226361 A1 | 8/2015 | Hernandez | |
| 2016/0053609 A1 * | 2/2016 | Nguyen | E21B 36/00 166/250.08 |
| 2016/0126118 A1 | 5/2016 | Chen et al. | |
| 2016/0146487 A1 | 5/2016 | Zywiak et al. | |
| 2016/0169825 A1 * | 6/2016 | Lehikoinen | F28F 27/00 165/11.2 |

FOREIGN PATENT DOCUMENTS

| | | |
|---|---|---|
| GB | 2292607 | 2/1996 |
| RU | 1776657 | 11/1992 |
| RU | 1778657 | * 11/1992 |
| WO | 2012132587 | 4/2012 |

OTHER PUBLICATIONS

PCT International Search Report from corresponding International Application PCT/US2014/045078, dated Nov. 6, 2014.
PCT Written Opinion of the International Searching Authority from corresponding International Application PCT/US2014/045078, dated Nov. 6, 2014.

* cited by examiner

HEAT EXCHANGER TESTING DEVICE

CROSS-REFERENCES TO RELATED APPLICATIONS

This application is a continuation-in-part of U.S. patent application Ser. No. 14/321,244 filed on Jul. 1, 2014, which claims priority to U.S. Provisional Patent Application No. 61/841,643 filed on Jul. 1, 2013, the entirety of both of which are incorporated herein.

BACKGROUND OF THE INVENTION

Heat exchangers often involve fluids flowing through conduits. The nature of the fluids passing through the heat exchangers and conduits, and the temperatures and other conditions present in the heat exchangers and conduits can lead to problems.

For example, various portions of the heat exchangers and conduits may become corroded as a result of the fluid, conditions or both. The corrosion can lead to leakage or breakage. Additionally, the heat exchangers and conduits may develop deposits as a result of materials in the fluid. The deposits may interfere with the flow of fluid through the heat exchangers and conduits and may also reduce the heat transfer capacity of same. Both of these problems are undesirable.

Many of these problems cannot be observed until after the heat exchanger has been online for some time. Furthermore, many of these problems can only be observed by removing and disassembling the heat exchanger and inspecting the conduits contained therein. The heat exchangers tend to be very large and can be quite costly. Additionally, removing the heat exchanger may require a process to shut down, which may impact a facility's production and output. Accordingly, it is crucial to avoid removing and disassembling a heat exchanger.

Therefore, it would be desirable to have an apparatus or process which allows for the materials of the conduits and the heat exchanger to be tested under nearly identical process conditions apart from the heat exchanger.

SUMMARY OF THE INVENTION

In one or more embodiments, the present invention provides a process and a device that can be placed inline with, or in a parallel line to, the fluid carrying conduits of the heat exchanger. The device can be subjected to the identical flow rates, temperatures, and other conditions of the heat exchangers that are used in the process (such as tube-and-shell heat exchangers) or other conduits. Accordingly, the testing device will be operated under nearly identical conditions as the heat exchangers in the plant or process. This will allow portions of the testing device to be disassembled and inspected for scale, corrosion and microbiological matter after a period of exposure time.

Therefore, in one aspect of the present invention, the invention provides a device for testing a heat exchanger configured to transfer heat to a first fluid, recover heat from the first fluid, or both. The device includes a test heat exchanger having a first inlet configured to receive the first fluid from the heat exchanger, a first outlet for the first fluid to the heat exchanger, a second inlet configured to receive a recirculating fluid, and, a second outlet for the recirculating fluid. The second outlet and the second inlet form a recirculation loop. The first fluid from the heat exchanger and the recirculating fluid are isolated fluidically. The device also includes a pump communicating with the test heat exchanger in the recirculation loop. Finally, the device includes a heater communicating with the test heat exchanger in the recirculation loop. The pump and the heater are configured to heat and circulate the recirculating fluid to adjust conditions in the test heat exchanger. The test heat exchanger, the pump and the heater are all disposed on a skid.

In at least one embodiment of the present invention, the test heat exchanger comprises a shell with at least one tube inside of the shell. Accordingly, it is contemplated that the first fluid from the heat exchanger flows inside of the at least one tube of the test heat exchanger and the recirculating fluid flows outside of the at least one tube. Alternatively, it is contemplated that the recirculating fluid flows inside of the at least one tube of the test heat exchanger and the first fluid from the heat exchanger flows outside of the at least one tube of the test heat exchanger.

In some embodiments of the present invention, the device includes a second test heat exchanger. The second test heat exchanger includes a first inlet configured to receive the first fluid from the heat exchanger, a first outlet for the first fluid from the heat exchanger, a second inlet configured to receive the recirculating fluid, and, a second outlet for the recirculating fluid. The first fluid from the heat exchanger and the recirculating fluid are isolated fluidically in the second test heat exchanger. It is contemplated that the first test heat exchanger comprises an inner tube in an outer tube and the second test heat exchanger comprises an inner tube in an outer tube. It is further contemplated that the inner tube of the first test heat exchanger comprises a first material, and the inner tube of the second test heat exchanger comprises a second material different than the first material.

In at least one embodiment of the present invention, the device includes at least one probe disposed in a conduit for the first fluid from the first heat exchanger, the recirculating fluid, or both.

In one or more embodiments of the present invention, an exterior portion of the test heat exchanger is semitransparent.

In another aspect of the present invention, the invention provides a process for testing a fluid from a conduit which includes: passing a portion of a first fluid from a heat exchanger to a test heat exchanger; circulating a second fluid through the test heat exchanger with a pump; and, heating the second fluid in a heater in order to control a temperature of the test heat exchanger, wherein the first fluid and second fluid are isolated fluidically.

In at least one embodiment, the test heat exchanger comprises a shell with at least one tube inside of the shell. Accordingly, it is contemplated that the process further includes passing the first fluid through the at least one tube of the test heat exchanger, and, passing the second fluid through the shell of the test heat exchanger and outside of the at least one tube of the test heat exchanger. Alternatively, it is contemplated that the process further includes circulating the second fluid through the at least one tube of the heat exchanger, and, passing the first fluid through the shell of the test heat exchanger and outside of the at least one tube of the test heat exchanger.

In at least one embodiment, monitoring a flow rate of at least one of the first fluid and the second fluid.

In one or more embodiments of the present invention, the process also includes passing at least a portion of the first fluid through a second test heat exchanger, circulating at least a portion of the second fluid through the second test heat exchanger with the pump, wherein the first fluid and second fluid are isolated fluidically in the second test heat exchanger, and, heating the second fluid in the heater to control a temperature of the second test heat exchanger. It is contemplated that the first test heat exchanger comprises an inner tube in an outer tube and the second test heat exchanger comprises an inner tube in an outer tube. It is further contemplated that the inner tube of the first test heat exchanger comprises a first material, and the inner tube of the second test heat exchanger comprises a second material different than the first material.

In some embodiments of the present invention, the process includes removing the test heat exchanger from the process. It is further contemplated that the process includes testing at least a portion of the test heat exchanger which had received the first fluid from the heat exchanger.

In at least one embodiment of the present invention, an exterior portion of the test heat exchanger is semitransparent.

According to another embodiment, the present invention provides a device for testing a fluid from a heat exchanger. The device includes test heat exchanger, a heater, and a skid. The test heat exchanger and the heater are disposed on the skid. The test heat exchanger includes a first inlet configured to receive the fluid from the heat exchanger, a first outlet for the fluid to the heat exchanger, a second inlet configured to receive a heat transfer fluid, and, a second outlet for the heat transfer fluid. The fluid from the heat exchanger and the heat transfer fluid are isolated fluidically within the test heat exchanger. The heater is in communication with the test heat exchanger and is configured to heat the heat transfer fluid.

It is contemplated that the test heat exchanger is a shell with at least one tube inside of the shell. The fluid from the heat exchanger flows inside of the at least one tube of the test heat exchanger and the heat transfer fluid flows outside of the at least one tube. Alternatively, the heat transfer fluid flows inside of the at least one tube of the test heat exchanger and the fluid from the heat exchanger flows outside of the at least one tube of the test heat exchanger.

It is also contemplated that the device includes a second test heat exchanger having a first inlet configured to receive the fluid from the heat exchanger, a first outlet for the fluid from the heat exchanger, a second inlet configured to receive the heat transfer fluid, and, a second outlet for the heat transfer fluid. The fluid from the heat exchanger and the heat transfer fluid are isolated fluidically in the second test heat exchanger. In various configurations, the first test heat exchanger includes an inner tube in an outer tube, and the second test heat exchanger includes an inner tube in an outer tube. In some configurations, the inner tube of the first test heat exchanger comprises a first material, and the inner tube of the second test heat exchanger comprises a second material different than the first material.

It is further contemplated that the device includes at least one probe disposed in a conduit for the fluid from the heat exchanger, the heat transfer fluid, or both.

It is contemplated that an exterior portion of the test heat exchanger is semitransparent.

It is contemplated that the device further includes a pump in communication with the test heat exchanger and configured to circulate the heat transfer fluid between the pump, the heater, and the test heat exchanger.

In still another embodiment, the present invention provides a device for testing a fluid from a heat exchanger which includes at least two test heat exchangers and a heater in communication with at least one of the test heat exchangers. The two test heat exchangers each include a first inlet configured to receive the fluid from the heat exchanger, a first outlet for the fluid to the heat exchanger, a second inlet configured to receive a heat transfer fluid, and, a second outlet for the heat transfer fluid. The fluid from the heat exchanger and the heat transfer fluid are isolated fluidically within each test heat exchanger. The heater is configured to heat the heat transfer fluid.

It is contemplated that the two test heat exchangers are both contained within a housing.

It is further contemplated that the two test heat exchangers each comprise a tube-in-tube heat exchanger. An outer portion of each tube-in-tube heat exchanger is at least semi-transparent.

It is also contemplated that the two test heat exchangers each are a tube-in-tube heat exchanger with an inner tube of the first test heat exchanger being a first material, and an inner tube of the second test heat exchanger being a second material different than the first material.

It is contemplated that the device further includes a pump in communication with the two test heat exchangers and configured to circulate the heat transfer fluid between the pump, the heater, and the two test heat exchangers.

It is still further contemplated that the heater is in communication with a first test heat exchanger, and the device includes a second heater in communication with a second test heat exchanger. It is further contemplated that each test heat exchanger has a first end and a second, opposite end. A heater is disposed at each end of both test heat exchangers.

In yet another embodiment, the present invention provides a device for testing a fluid from a heat exchanger, which includes a test heat exchanger and a heater in communication with the test heat exchanger. The test heat exchanger includes a first inlet configured to receive the fluid from the heat exchanger, a first outlet for the fluid to the heat exchanger, a second inlet configured to receive a heat transfer fluid, and, a second outlet for the heat transfer fluid. The fluid from the heat exchanger and the heat transfer fluid are isolated fluidically within the test heat exchanger. Additionally, the test heat exchanger includes an inner tube within an outer tube. An outer portion of the test heat exchanger is semitransparent. The heather is configured to heat the heat transfer fluid.

It is contemplated that the device includes a second test heat exchanger having a first inlet configured to receive the fluid from the heat exchanger, a first outlet for the fluid to the heat exchanger, a second inlet configured to receive a heat transfer fluid, and, a second outlet for the heat transfer fluid. The fluid from the heat exchanger and the heat transfer fluid are isolated fluidically within the second test heat exchanger. The second test heat exchanger is an inner tube within an outer tube. An outer portion of the second test heat exchanger is semitransparent. Additionally, it is contemplated that the device includes a second heater in communication with the second test heat exchanger. The second heater is configured to heat the heat transfer fluid of the second test heat exchanger.

These and other embodiments and aspects of the present invention will be appreciated by those of ordinary skill in the art based upon the following description of some of the embodiments and aspects of the present invention.

BRIEF DESCRIPTION OF THE DRAWINGS

The figures in the appended drawing will make it possible to understand how the invention can be produced. In these figures, similar reference numbers denote similar elements.

DETAILED DESCRIPTION OF THE PREFERRED EMBODIMENTS

Figure 1:
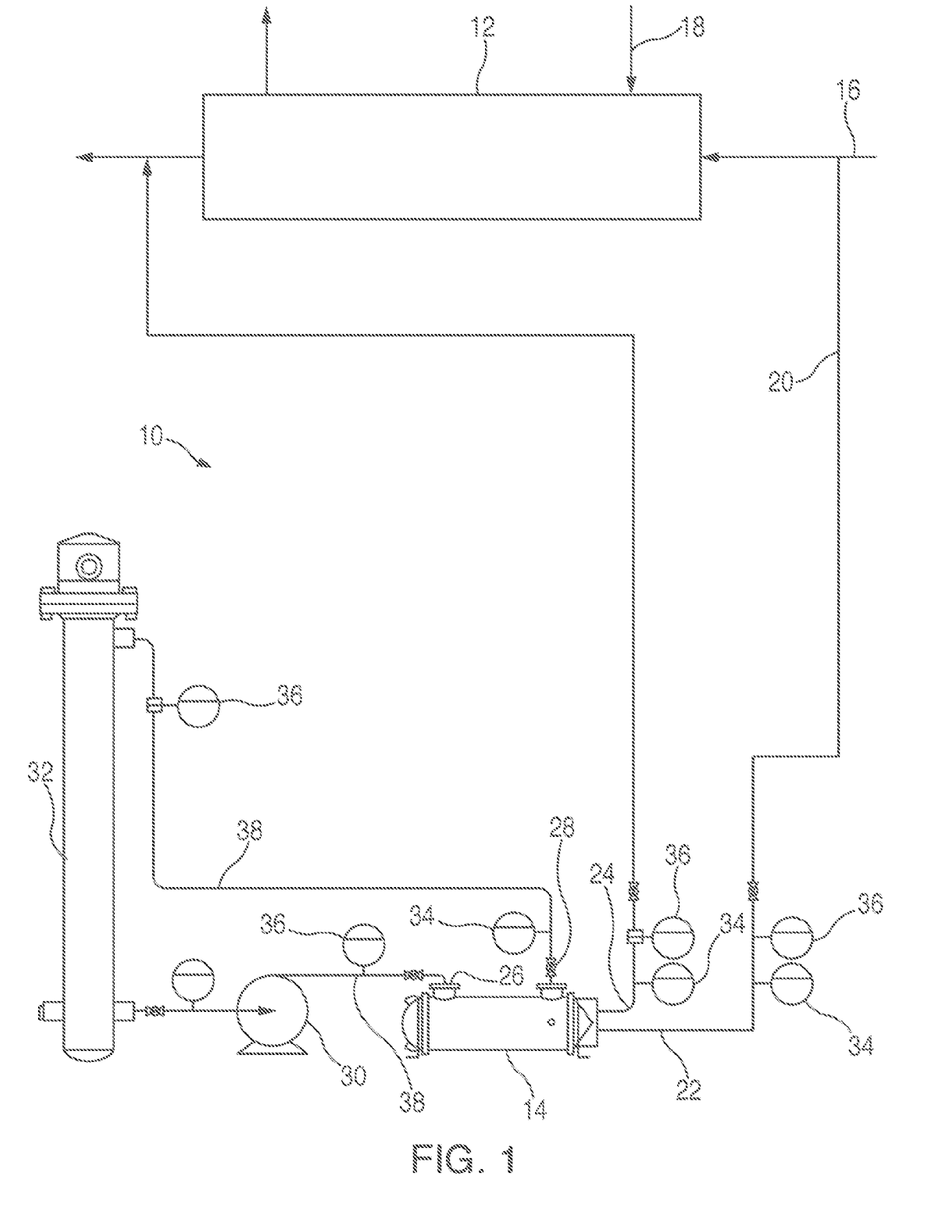
FIG. 1 is a schematic view of a device according to an embodiment of the present invention.

With reference to FIG. 1, a device 10 according to one or more embodiments of the present invention is shown which include a first heat exchanger 12 and a test heat exchanger 14. The first heat exchanger 12 receives a first fluid, for example via a line 16, and recovers heat from the first fluid, or passes heat to the first fluid, or both. Typically, the first heat exchanger 12 also receives another fluid, for example, via a line 18, which can supply heat to the first fluid or receive heat from the first fluid. These heat exchangers 12 are known.

In order to test the materials of the first heat exchanger 12, a portion of the first fluid is passed, via a line 20, to the test heat exchanger 14. Accordingly, the test heat exchanger 14 has an inlet 22 for the first fluid and an outlet 24 to return the first fluid to the first heat exchanger 12. The first fluid may be combined with fluid exiting the first heat exchanger 12, and it would still be considered returning the first fluid to the first heat exchanger 12.

As shown in FIG. 1, the test heat exchanger 14 also has an inlet 26 for a recirculating fluid and an outlet 28 for the recirculating fluid. Within the test heat exchanger 14, the first fluid and the recirculating fluid do not come into fluid contact (i.e., the two are isolated fluidically). In one embodiment of the present invention the recirculating fluid is glycol, however any other such fluids, such as water, may be used.

The recirculating fluid is circulated into and out of the test heat exchanger 14 via a pump 30 in a recirculation loop. In order to adjust the temperature of the recirculating fluid, the device 10 includes a heater 32. The heater 32 may be used to adjust the temperature of the recirculating fluid, which in turn will adjust the temperature in the test heat exchanger 14 to have similar operating conditions to the first heat exchanger 12.

Appropriate temperature sensors 34 are used to maintain the skin temperature of the test heat exchanger 14 at a temperature approximately equal to the skin temperature of the first heat exchanger 12. Additionally, flow meters 36 are provided in at least one line 38 to allow for appropriate calculations of erosion and scale deposit which may be extrapolated from the test period of operation of the test heat exchanger 14.

The test heat exchanger 14 of the device 10 can be operated for a predetermined period of time. For example, the device 10 can be operated for an amount of time that is sufficient to determine corrosion levels in the first heat exchanger 12 by extrapolating the data from the test heat exchanger 14. In order to view the corrosion, mineral deposits, or other problems that may arise, the test heat exchanger 14 can be removed from the device 10 and opened for visual inspection. If needed, one or more portions of the test heat exchanger 14 can be destructively tested.

Figure 2A:
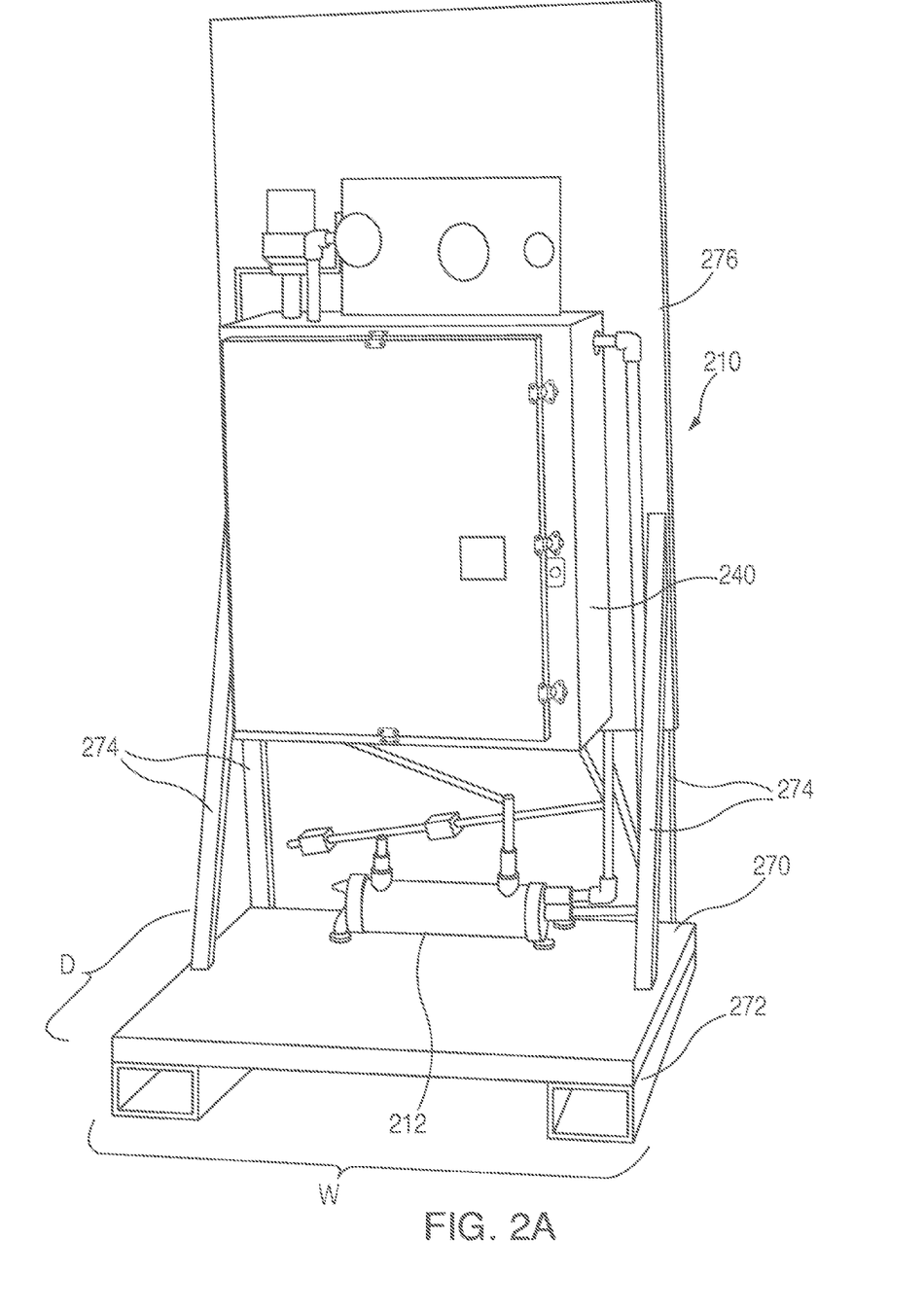
FIG. 2A is front perspective view of a device according to one or more embodiments of the present invention.
Figure 2B:
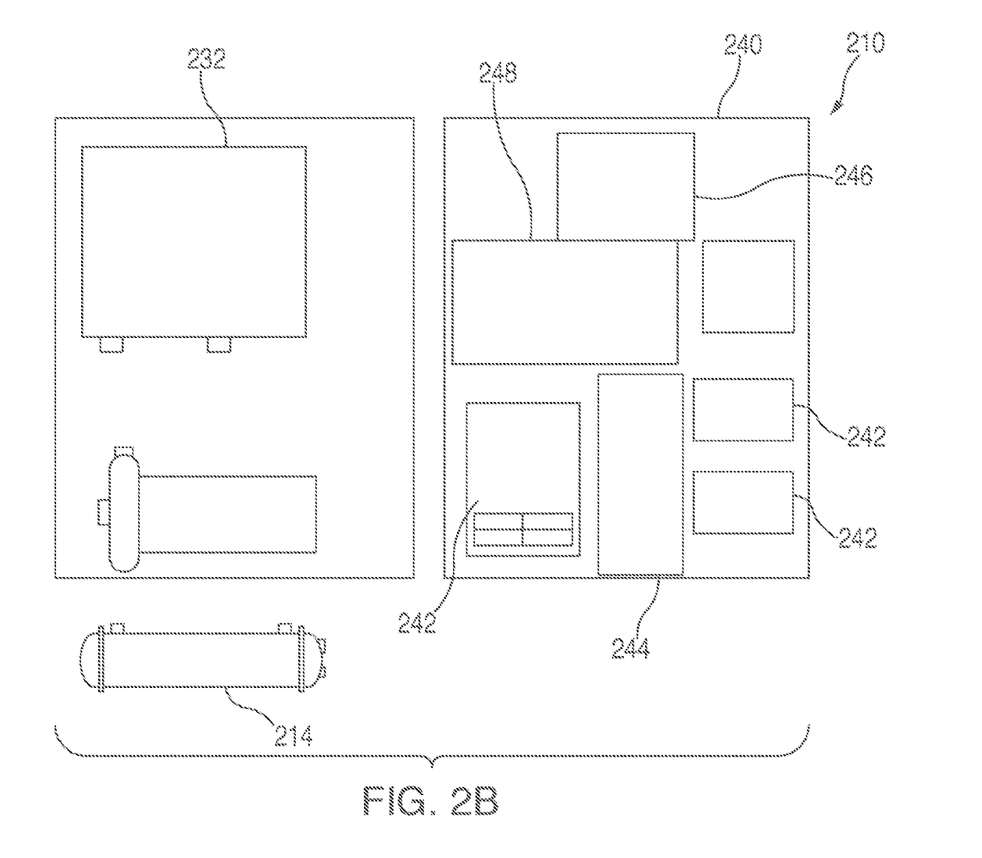
FIG. 2B is a schematic view of a portion of the device shown in FIG. 2A.

Another embodiment of the present invention is shown in FIGS. 2A and 2B in which components which are similar to the ones described above, have similar reference numerals with the exception of a preceding "2."

As shown in this embodiment, the device 210 includes a test heat exchanger 212 and a housing 240 mounted on a skid 270. Although not shown, a pump and a heater are disposed inside of the housing 240 (see FIG. 2B, below). The skid 270, or movable platform, includes a base 272, supports 274, and a backing 276. The base 274 of the skid 270 has a width W of approximately 0.91 meters (36 inches) and a depth D of approximately 1.1 (42 inches). For example, the base 274 of the skid 270 may be sized so that the device 210, including the test heat exchanger 212, can be moved with a pallet jack or other similar devices for moving pallets. Such a device 210 can be easily placed near operating heat exchangers and placed online for the testing period. Once the testing period is completed, the device 210 can be taken offline, inspected, and, if desired, moved to another location for testing.

As shown in FIG. 2B, a potential equipment layout arrangement for the housing 240 according to one embodiment includes a pump 230 typically driven by a motor, and a heater 232. Various electrical components of the device are shown as also being contained in the housing 240 including various circuit breakers 242, transformers 244, switches, input/output devices 246, and instrumentation 248. The input/output devices 246 can be, for example, a touch screen which displays information associated with the temperature sensors 32 or flow meters 36. See, FIG. 1. Additionally, the input/output devices 246 can allow for control of the heater 232 to adjust the temperature or adjust valves (discussed below) to control the flow of fluids in the device.

Figure 3A:
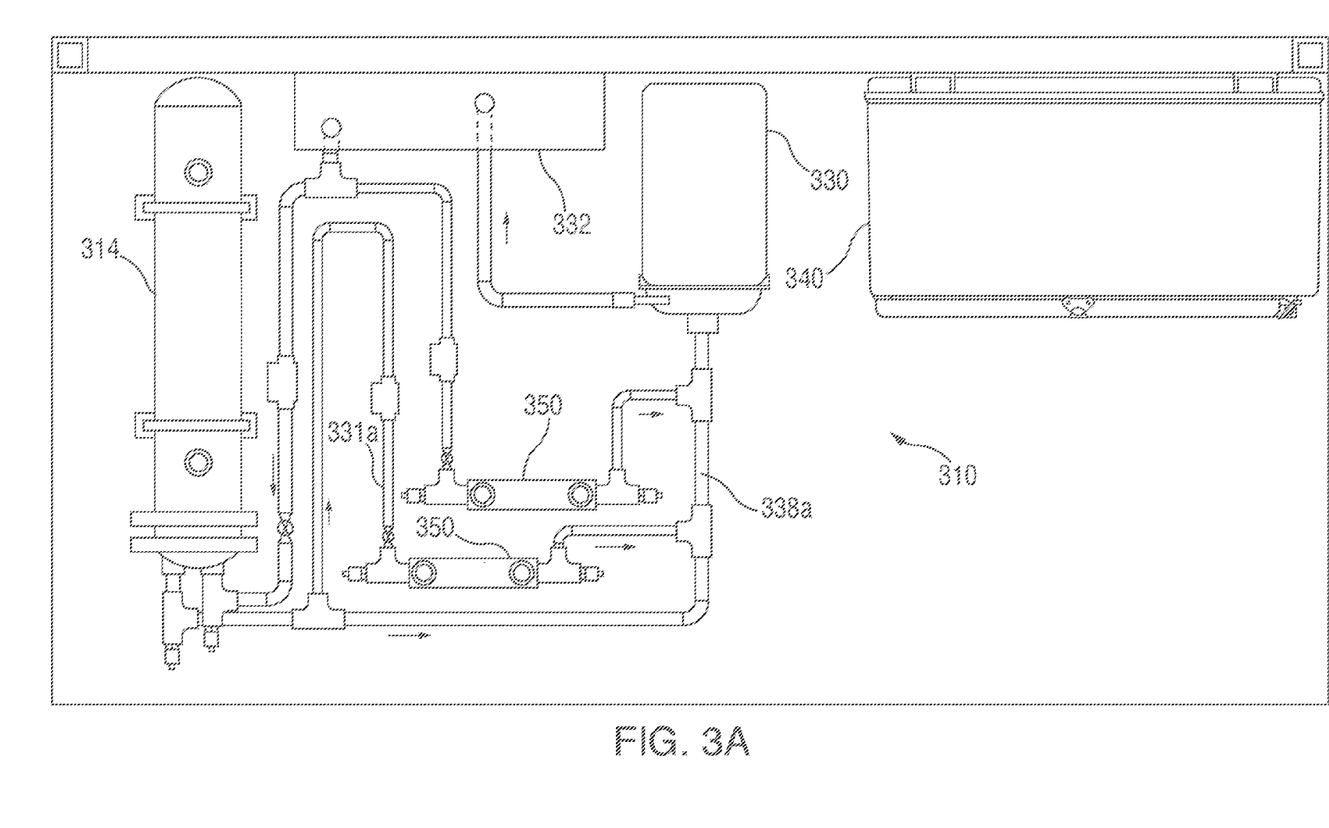
FIG. 3A is a top view of a device according to an embodiment of the present invention showing conduit lines for a recirculating fluid.
Figure 3B:
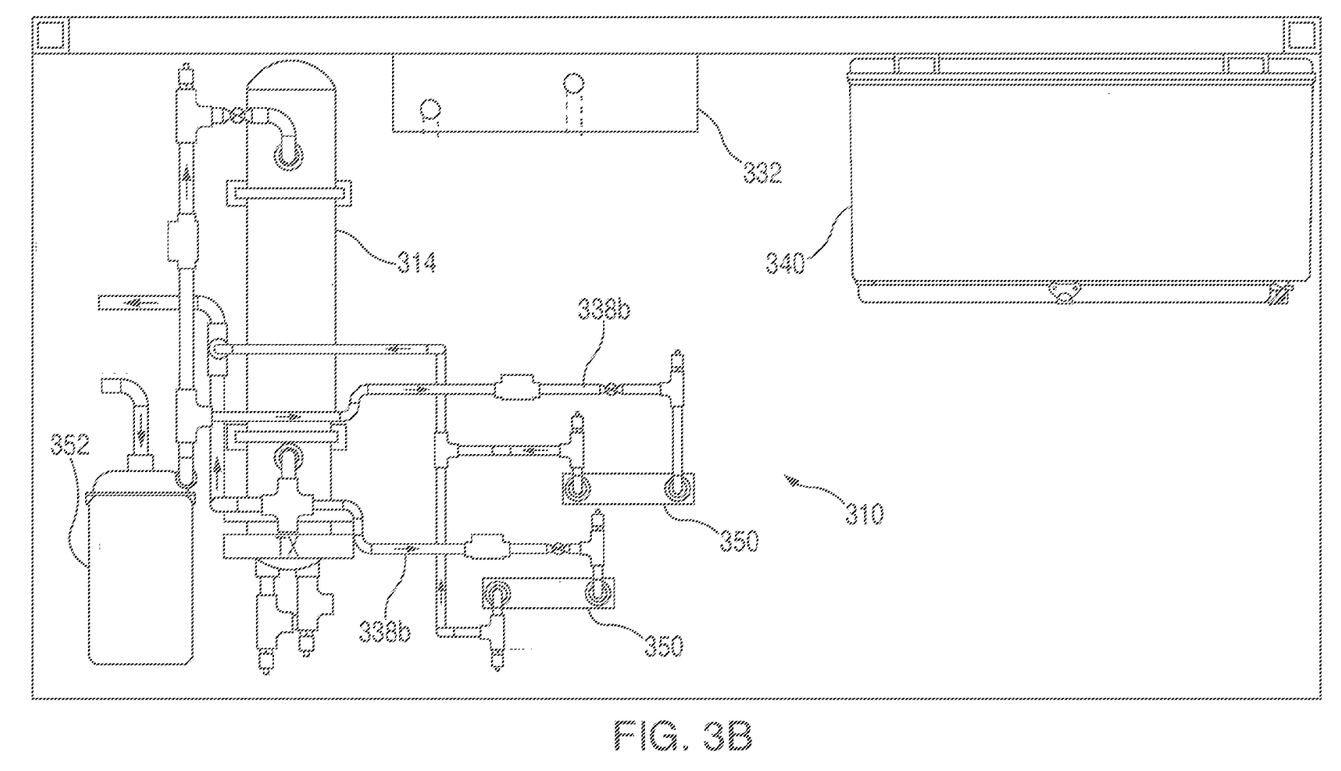
FIG. 3B is a top view of the device shown in FIG. 3A showing conduit lines for a fluid from a heat exchanger.

Another embodiment of the present invention is shown in FIGS. 3A and 3B in which components which are similar to the ones described above, have similar reference numerals with the exception of a preceding "3."

As shown in this embodiment, the device 310 includes one or more testing probes 350 disposed in, for example, conduits 338a for the second fluid. In a preferred embodiment, the testing probe 350 is capable of testing both the first fluid and the recirculating fluid.

In FIG. 3A, for example, the probe 350 is disposed within a conduit 338a for the recirculating fluid. As can be seen in FIG. 3B, the probe 350 also receives a portion of the first fluid via conduits 338b. The probes 350 can provide, for example, pH values, ionic data, or other data about the first fluid or the recirculating fluid.

Additionally, as can be seen in FIG. 3B, in this embodiment, the device 310 includes a second pump 352. The second pump 352 moves the first fluid throughout the device 310, including the probes 350, in order to avoid any pressure drop.

Figure 4:
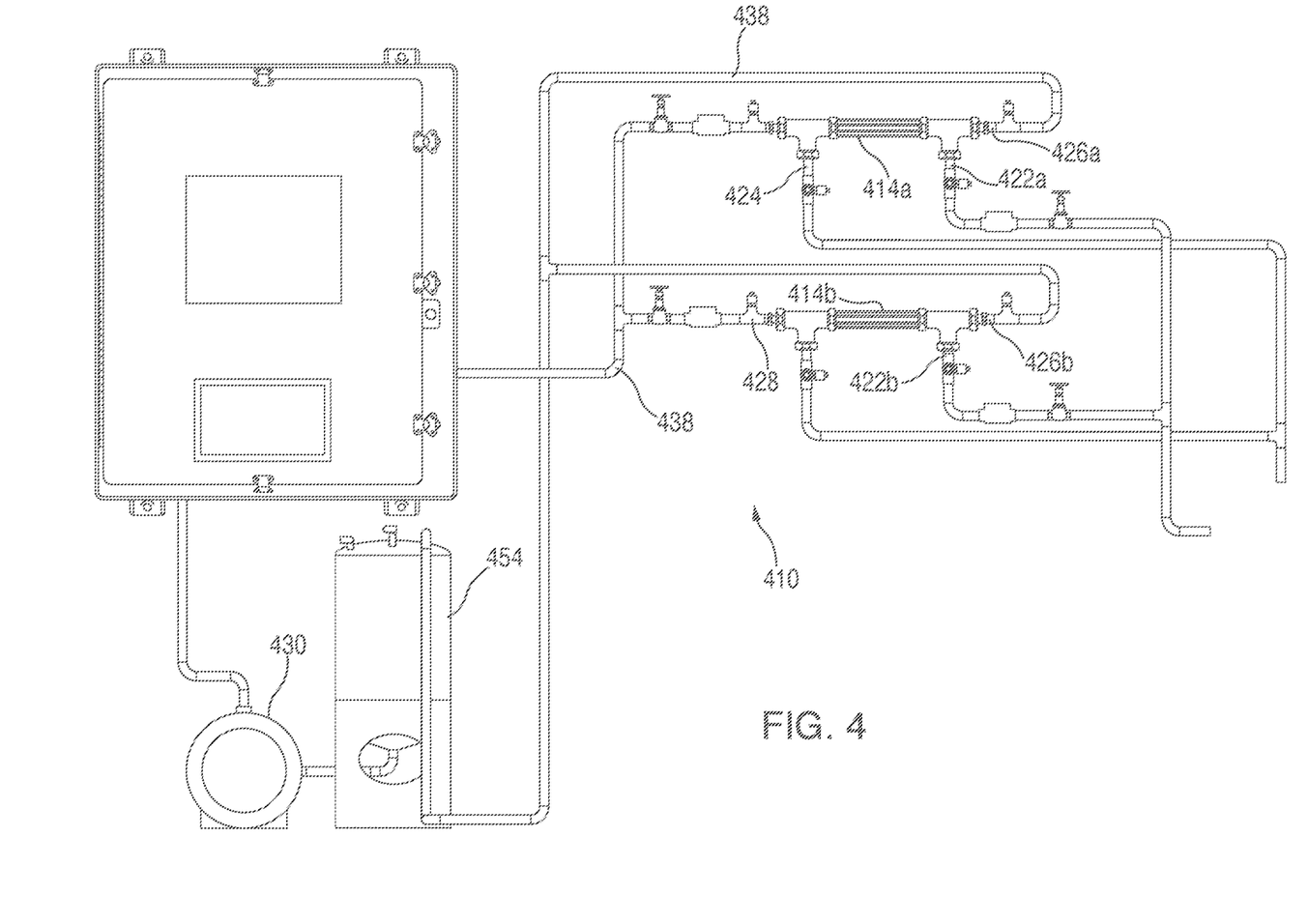
FIG. 4 is a front view of a device according to an embodiment of the present invention.

Accordingly, another embodiment is shown in FIG. 4 in which components which are similar to the ones described above, have similar reference numerals with the exception of a preceding "4."

As depicted in FIG. 4, a device 410 includes two test heat exchangers 414a, 414b which are arranged in parallel. It is also contemplated that the test heat exchangers 414a, 414b could be arranged in series. Each test heat exchanger 414a, 414b receives a portion of the first fluid via inlets 422a, 422b and a portion of the recirculating fluid via inlets 426a, 426b. By utilizing more than one test heat exchanger 414a, 414b, different materials, such as metals, metal alloys, or other materials typically used or conditions can be evaluated at the same time.

Additionally, as shown in FIG. 4, this embodiment of the device 410 includes a tank 454 which operates as a reservoir for recirculating fluid. If needed, additional fluid can be withdrawn from the tank 454.

Figure 5:
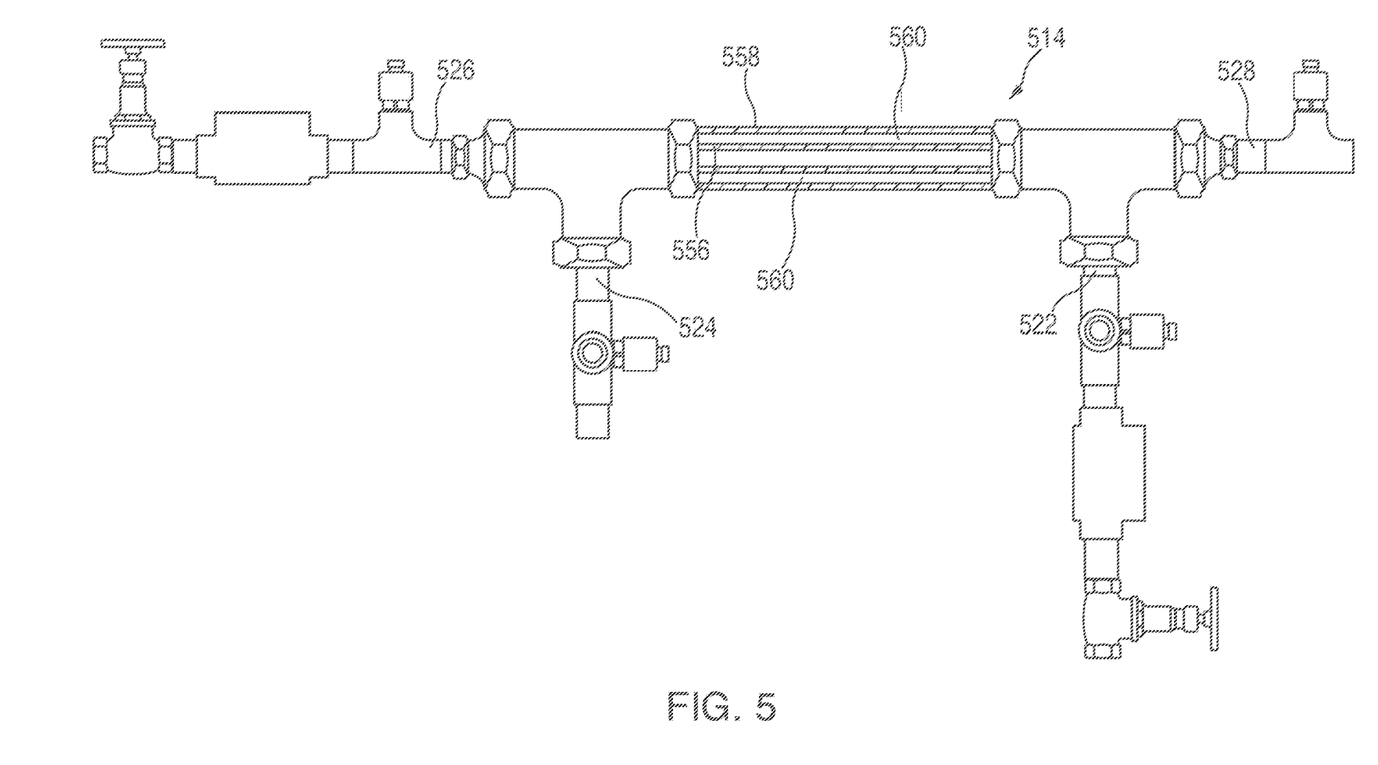
FIG. 5 is a side partial cutaway view of a heat exchanger used in one or more embodiments of the present invention.
Figure 6:
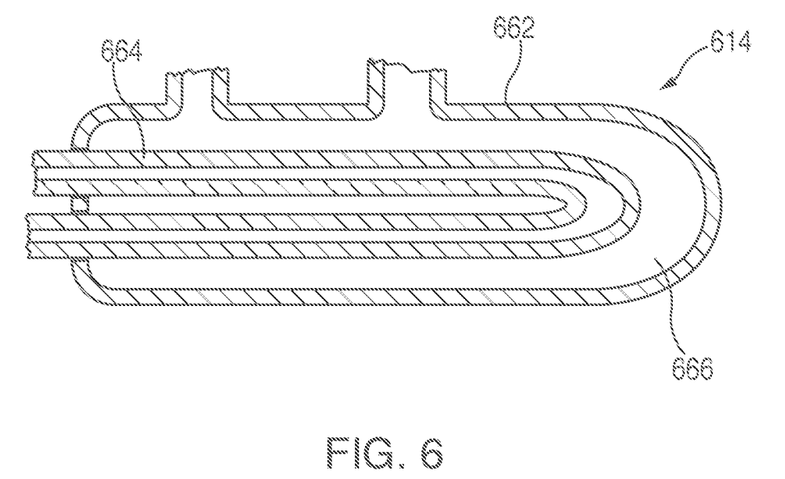
FIG. 6 is a side cutaway view of another heat exchanger used in one or more embodiments of the present invention.

FIGS. 5 and 6 depicted various designs for the test heat exchangers that may be utilized in the various embodiments of the present invention.

In FIG. 5, for example, a test heat exchanger 514 is shown which comprises a tube-in-tube design. The tube-in-tube test heat exchanger 514 includes an inner tube 556 and an outer tube 558. One fluid flows inside of the inner tube 556, and the second fluid flows in a space 560 between the inner tube 556 and the outer tube 558. It is contemplated that a portion of a heat exchanger 514, for example the outer tube 558, is at least semi-transparent to allow for visual inspection while the device is operating.

As shown for example in FIG. 6, a test heat exchanger 614 comprises a tube-and-shell heat exchanger 614. The tube-and-shell heat exchanger 614 comprises an outer shell 662 with at least one tube 664 inside of the shell 662. A first fluid flows in the at least one tube 664, while the second flows in a space 666 between the shell 662 and the at least one tube 664.

For example, the recirculated fluid may flow in the space 666 between the shell 662 and the at least one tube 664, while the first fluid flows with the at least one tube 664. Alternately, the recirculated fluid may flow through the at least one tube 664 and the first fluid may flow in the space 666 between the shell 662 and the at least one tube 664.

As will be appreciated other designs for the test heat exchanger may be used in which the test heat exchanger allows for the conditions of the test heat exchanger to reproduce the conditions of the heat exchanger.

Figure 7:
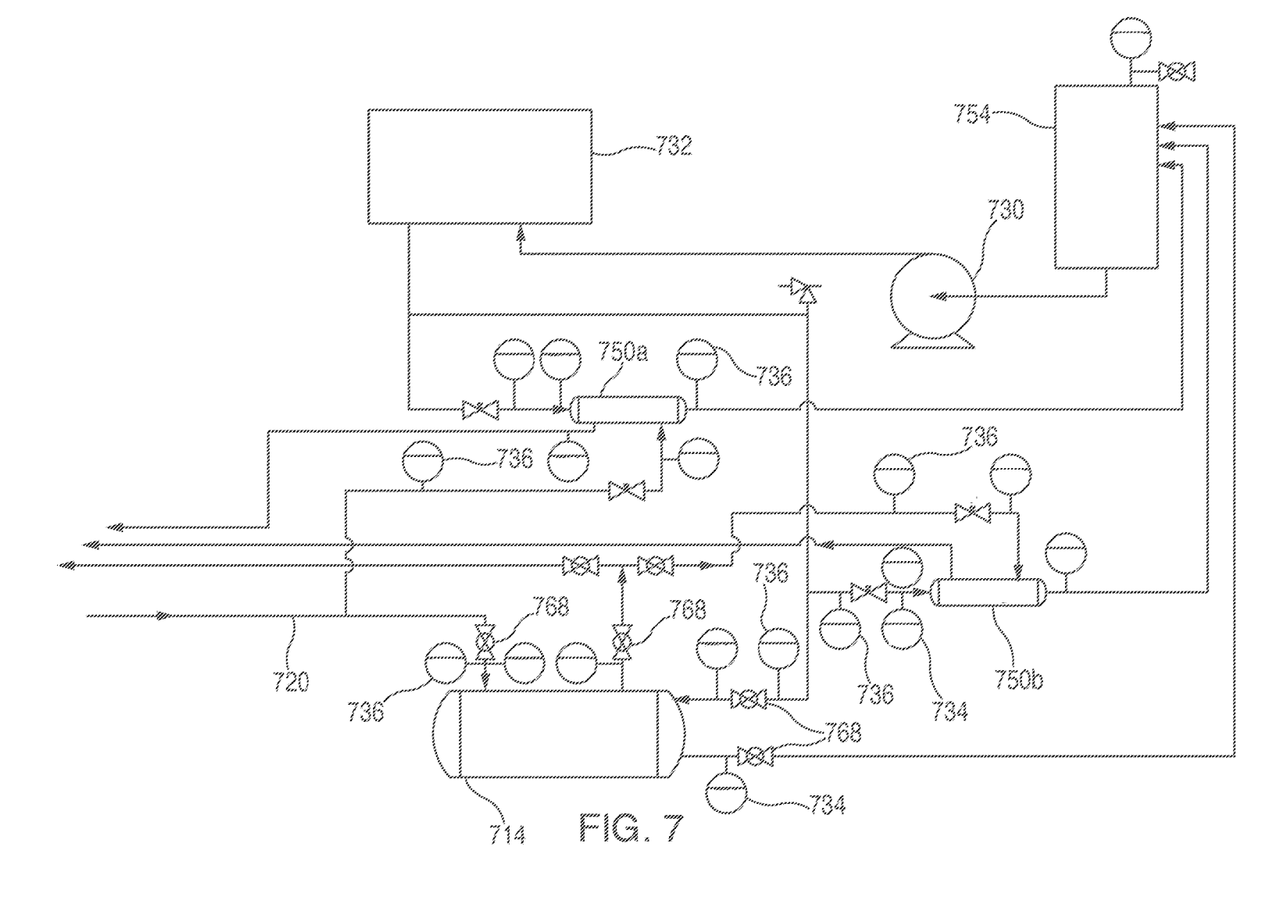
FIG. 7 is a process flow diagram according to one or more embodiments of the present invention.

With reference to FIG. 7, in which components which are similar to the ones described above, have similar reference numerals with the exception of a preceding "7," an exemplary process according to the present invention will be described.

A portion of the first fluid which is passed to a heat exchanger is passed via a line 720 to at least one test heat exchanger 714. The first fluid in line 720 preferably is a slip stream of a conduit passing the first fluid into the heat exchanger, although other configurations may also be employed. A portion of the first fluid may also be passed to a first probe 750a to obtain, for example, electrochemical or other conditions of the first fluid.

The first fluid is passed through test heat exchanger 714. Upon exiting the test heat exchanger 714, the first fluid may be passed back to the heat exchanger. It is contemplated that a portion of the first fluid after it exits the test heat exchanger 714 may be passed to a second probe 750b to obtain, again, for example, electrochemical or other conditions of the first fluid. The first fluid could be returned upstream to the heat exchanger or downstream of the heat exchanger.

In addition to the first fluid, the test heat exchanger 714 receives a recirculating fluid that is passed in a recirculation loop via a pump 730. Accordingly, recirculating fluid may be passed from a tank 754 to a heater 732 to obtain a desired temperature. Once the recirculating fluid has been heated, the recirculating fluid is passed to the test heat exchanger 714. After passing through the test heat exchanger 714, the recirculating fluid may be returned to the tank 754. A portion of the recirculating fluid exiting the test heat exchanger 714 may also be passed to each of the probes 750a, 750b.

Flow meters 736 and temperature sensors 734 may be used to monitor the flow rates and temperatures of the fluids at various positions in the process. Valves 768 and the heater 732 can be used to adjust the temperature(s) and flow rate(s) into and out of the test heat exchanger 714 so that it is equivalent to the operating conditions of the heat exchanger. Additionally, the temperature(s) and flow rate(s) can be adjusted to allow for the testing of different operating conditions in each test heat exchanger to allow for simultaneous testing. Furthermore, in devices and process with multiple heat exchangers, the different heat exchangers can include different materials, different operating conditions or both, to allow the testing of multiple conditions and materials at the same time.

After an amount of time that is preferably predetermined to be sufficient, any of the test heat exchangers can be taken offline and inspected at a fraction of the cost of the heat exchanger. Further, there is minimal, if any, impact on the heat exchanger operations as it can continue to be operated while the test heat exchanger is being inspected and potentially subjected to destructive testing. Thus, in addition to avoiding the destruction of the expense heat exchanger, the devices and processes of the present invention allow the process using the heat exchangers to continue operations while the test heat exchanger is removed, inspected and tested.

Figure 8:
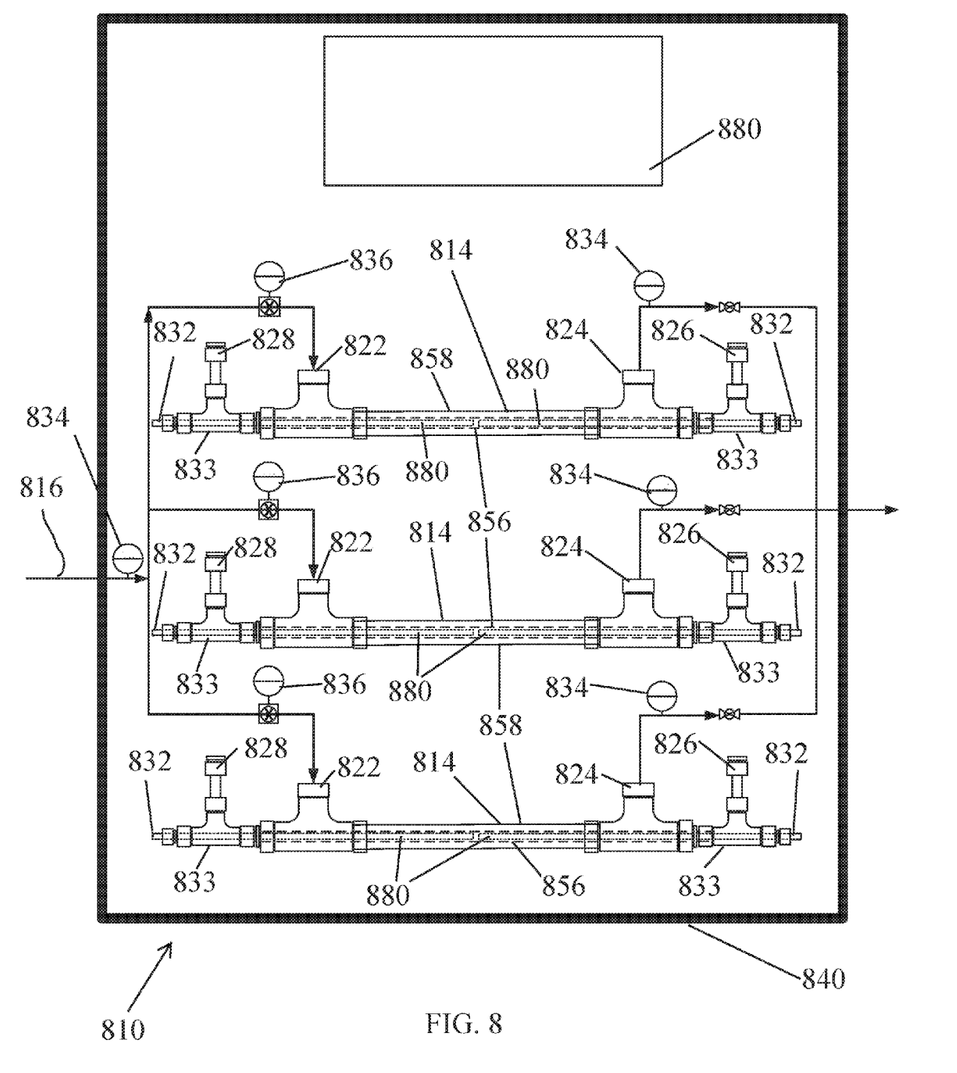
FIG. 8 is a schematic view of another device according to one or more embodiments of the present invention.
Figure 9:
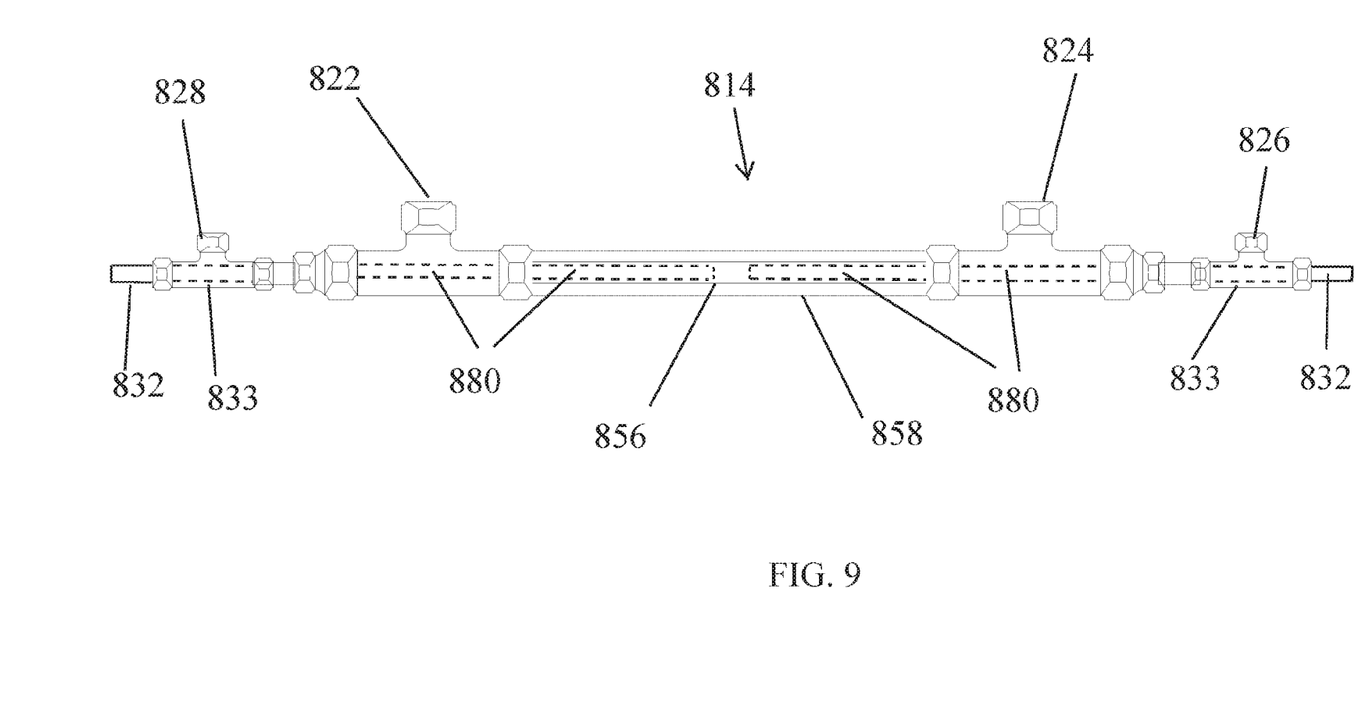
FIG. 9 is a side partial cutaway view of another heat exchanger used in one or more embodiments of the present invention.

Turning to FIGS. 8 and 9, another embodiment of the present invention is shown in which components which are similar to the ones described above, have similar reference numerals with the exception of a preceding "8."

In FIG. 8, a heat exchanger testing device 810 is shown in which three test heat exchangers 814 are contained with a housing 840. The housing 840 can be made from any suitable material, such as, for example, metal.

Each of the test heat exchangers 814 comprise a tube-in-tube design in which the outer tube 858 surrounds the inner tube 856. Preferably, the outer tube 858 is at least partially transparent as discussed above. Additionally, each of the test heat exchangers 814 includes an inlet 822 for the first fluid and an outlet 824 for the first fluid. As with the previous embodiments, the first fluid is fluid that is typically used in the heat exchanger 12 (FIG. 1) that is being inspected with the testing device 810. As would be appreciated, the configuration and relationship shown in FIG. 1 between the heat exchanger 12 and the test heat exchanger 14 is merely exemplary to illustrate that both receive the first fluid. The test heat exchangers 814 also include an inlet 826 and an outlet 828 for the second fluid, which comprises the heat transfer fluid, such as water, glycol, or a mixture thereof.

The heat exchanger testing device 810 also various includes temperature sensors 824 and flow meters 836. Circuitry 880 is contained within the housing 840 of the heat exchanger testing device 810 and includes a processor, memory, and/or hardware (e.g., ports, interfaces, antennas, amplifiers, signal processors, etc.) for wired or wireless communication. The circuitry 880 may also include software stored in a non-transitory medium, hardware, firmware, etc., containing executable instructions for causing the heat exchanger testing device 810 or components thereof to perform one or more steps, to receive data from one or more instruments, such as the temperature sensors 824 and flow meters 836 and/or transmit data, via a wired or wireless communication method. Example software can include an operating system running one or more applications (apps) that perform one or more steps of example methods. Existing operating systems or apps may be configured to cause circuitry 880 to perform steps of example methods.

The transmission of the data can be a wireless transmission (for example by WiFi) or a wired transmission (for example using an Ethernet RJ45 cable or an USB cable). For a wireless transmission (for example, Bluetooth, WiFi, LiFi, 4G or 5G or future generation mobile network), a wireless transceiver (for example a WiFi transceiver) is connected to a communication port of the circuitry 880. The transmission can be performed automatically, at the request of the circuitry 880, in response to a request from another device, or in other ways. A request can be generated in response to a received input, or generated automatically. Additionally, the circuitry 880 is in communication with at least one heater 832.

As shown in FIGS. 8 and 9, in this embodiment, each test heat exchanger 814 is associated with at least one heater 832. In the preferred embodiment, each test heat exchanger 814 is associated with two heaters 832, one at each end of the test heat exchanger 814 as shown in FIGS. 8 and 9. Specifically, a "T" coupling 833 is disposed at each end of the test heat exchanger 814. The heaters 832 comprise a rod 880 that extends through a "T" coupling 833 and into the inner tube 856 of the test heat exchanger 814. The heat transfer fluid is contained with the "T" couplings 833 and the inner tubes 856 and surrounds the rod 880 of the heater 832. Exemplary heaters 832 that are contemplated to be used are available from Watlow Electric Manufacturing Co., in St. Louis, Mo.

The "T" couplings 833 can be closed, meaning that heat transfer fluid does not circulate out of the test heat exchanger 814 and the "T" couplings 833. Such a configuration eliminates the need for a pump, and reduces the required electrical demand of the testing device 810. However, it is also contemplated that the heat transfer fluid is circulated between the various test heat exchangers 814 via the "T" couplings 833—with one "T" coupling 833 functioning as an inlet for the heat transfer fluid and one T" coupling functioning as an outlet for the heat transfer fluid.

In use, the heat transfer fluid is heated by one of the heaters 832 disposed at the ends of the test heat exchangers 814. The (heated) heat transfer fluid heat the inner surface of the inner tube 856. The first fluid, in the outer tube 858, contacts the outer surface of the inner tube 856 and absorbs heat to achieve the desired conditions within the test heat exchanger 814, for example to mimic the conditions (e.g., the skin temperature) of the heat exchanger 12.

The temperature of the heaters 832 can be set as a group or individually. The circuitry 880 includes controls configured to adjust the temperature of the heaters 832, or each heater 832 may include its own controller. Additionally, the temperatures can all be the same or they can be different. By using different temperatures for some of the heaters 832, different conditions can be created in different heat exchangers 814 of the testing device 810. As will be appreciated, by providing different conditions with the test heat exchangers 814, different operating conditions can be utilized simultaneously.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The invention claimed is:

1. A device for testing a fluid from a heat exchanger, the device comprising:
    a first test heat exchanger comprising a first inlet configured to receive a first portion of the fluid from the heat exchanger, a first outlet for the first portion of the fluid from the heat exchanger, a second inlet configured to receive a heat transfer fluid, and, a second outlet for the heat transfer fluid, wherein the first portion of the fluid from the heat exchanger and the heat transfer fluid are isolated fluidically within the first test heat exchanger;
    a first heater in communication with the first test heat exchanger, the first heater configured to heat the heat transfer fluid; and,
    a second test heat exchanger comprising a first inlet configured to receive a second portion of the fluid from the heat exchanger, a first outlet for the second portion of the fluid from the heat exchanger, a second inlet configured to receive a heat transfer fluid, and, a second outlet for the heat transfer fluid, wherein the second portion of the fluid from the heat exchanger and the heat transfer fluid are isolated fluidically within the second test heat exchanger; and,
    a second heater in communication with the first test heat exchanger, the first heater configured to heat the heat transfer fluid.

2. The device of claim 1, wherein the first test heat exchanger and the second test heat exchanger both comprise a shell with at least one tube inside of the shell.

3. The device of claim 2, wherein the first and second portions of the fluid from the heat exchanger, respectively, flows inside of the at least one tubes of the first and second test heat exchangers and the heat transfer fluid flows outside of the at least one tubes of the first and second test heat exchangers.

4. The device of claim 2, wherein the heat transfer fluid flows inside of the at least one tubes of the first and second test heat exchangers and the first and second portions of the fluid from the heat exchanger, respectively, flows outside of the at least one tubes of the first and second test heat exchangers.

5. The device of claim 1 wherein the heat transfer fluid is recirculated between the first and second test heat exchangers.

6. The device of claim 1, wherein the first test heat exchanger comprises an inner tube in an outer tube, and wherein the second test heat exchanger comprises an inner tube in an outer tube, and wherein the inner tube of the first test heat exchanger comprises a first material, and the inner tube of the second test heat exchanger comprises a second material different than the first material.

7. The device of claim 1 further comprising:
    at least one probe disposed in a conduit for the fluid from the heat exchanger, the heat transfer fluid, or both.

8. The device of claim 1, wherein an exterior portion of the at least one of the first and second test heat exchangers is semitransparent.

9. The device of claim 1 further comprising a pump in communication with the test heat exchanger and configured to circulate the heat transfer fluid between the pump, the heater, and the first and second test heat exchangers.

10. The device of claim 1 wherein the heat transfer fluid is not circulated between the first and second test heat exchangers.

11. A device for testing a fluid from a heat exchanger, the device comprising:
- at least two test heat exchangers, each test heat exchanger comprising a first inlet configured to receive the fluid from the heat exchanger, a first outlet for the fluid to the heat exchanger, a second inlet configured to receive a heat transfer fluid, and, a second outlet for the heat transfer fluid, wherein the fluid from the heat exchanger and the heat transfer fluid are isolated fluidically within each test heat exchanger,
- wherein each test heat exchanger has a first end and a second, opposite end, and wherein a heater is disposed at each end of both test heat exchangers such that a first and second heater are in communication with a first test heat exchanger from the at least two test heat exchangers, and wherein a third and fourth heaters are in communication with a second test heat exchanger from the at least two test heat exchangers; and,
- wherein each heater is
- configured to heat the heat transfer fluid.

12. The device of claim 11, wherein the at least two test heat exchangers are both contained within a housing.

13. The device of claim 11, wherein the at least two test heat exchangers each comprise a tube-in-tube heat exchanger, and wherein an outer portion of each tube-in-tube heat exchanger is at least semi-transparent.

14. The device of claim 11, wherein the at least two test heat exchangers each comprise a tube-in-tube heat exchanger, and an inner tube of a first test heat exchanger comprising a first material, and an inner tube of the second test heat exchanger comprising a second material different than the first material.

15. The device of claim 11, further comprising a pump in communication with the at least two test heat exchangers and configured to circulate the heat transfer fluid between the pump, the heater, and the at least two test heat exchangers.

16. The device of claim 11 wherein each of the at least two heat exchangers include a closed coupling at both the first and second ends.

17. The device of claim 11 wherein each of the at least two heat exchangers include a coupling at both the first and second ends, and wherein the couplings at the first end are configured as inlets for the heat transfer fluid, and wherein the couplings at the second end are configured as outlets for the heat transfer fluid.

* * * * *